(12) United States Patent
Vallana et al.

(10) Patent No.: US 6,447,439 B1
(45) Date of Patent: Sep. 10, 2002

(54) DEVICE FOR CONVEYING RADIOACTIVE AGENTS ON ANGIOPLASTY STENTS, RESPECTIVE METHOD AND KIT

(75) Inventors: Franco Vallana; Benito Chinaglia, both of Turin; Maria Curcio, Vercelli; Giovanni Rolando, Turin, all of (IT)

(73) Assignee: Sorin Biomedica Cardio S.p.A. (IT)

( * ) Notice: Subject to any disclaimer, the term of this patent is extended or adjusted under 35 U.S.C. 154(b) by 0 days.

(21) Appl. No.: 09/692,373

(22) Filed: Oct. 19, 2000

(30) Foreign Application Priority Data

Nov. 23, 1999 (EP) .............................. 99830721

(51) Int. Cl.$^7$ .......................... A61N 5/00; A61M 29/00
(52) U.S. Cl. ........................ 600/3; 604/101.01
(58) Field of Search .............. 424/1.25; 600/3, 600/4; 604/101.01

(56) References Cited

U.S. PATENT DOCUMENTS

| | | | |
|---|---|---|---|
| 4,349,498 A | 9/1982 | Ellis et al. | ............. 264/81 |
| 4,503,569 A | 3/1985 | Dotter | |
| 4,768,507 A | 9/1988 | Fischell et al. | |
| 4,776,337 A | 10/1988 | Palmaz | |
| 4,800,882 A | 1/1989 | Gianturco | |
| 4,819,618 A | 4/1989 | Liprie | |
| 4,830,003 A | 5/1989 | Wolff et al. | |
| 4,856,516 A | 8/1989 | Hillstead | |
| 4,886,062 A | 12/1989 | Wiktor | |
| 4,907,336 A | 3/1990 | Gianturco | |
| 5,059,166 A | 10/1991 | Fischell et al. | |

(List continued on next page.)

FOREIGN PATENT DOCUMENTS

| | | |
|---|---|---|
| DE | 196 00 669 A1 | 8/1996 |
| EP | 0 433 011 A1 | 6/1991 |
| EP | 0 540 290 A2 | 5/1993 |
| EP | 0 593 136 A1 | 4/1994 |
| EP | 0 797 963 A2 | 10/1997 |
| EP | 0 806 190 A1 | 11/1997 |
| EP | 0 847 766 A2 | 6/1998 |
| EP | 0 850 604 A2 | 7/1998 |
| EP | 0 857 470 A2 | 8/1998 |
| EP | 0 873 732 A1 | 10/1998 |
| EP | 0 875 215 A1 | 11/1998 |
| EP | 0 895 759 A1 | 2/1999 |
| EP | 0 895 760 A1 | 2/1999 |
| WO | WO 96/03092 A1 | 2/1996 |
| WO | WO 97/21399 | 6/1997 |
| WO | WO 98/48851 | 11/1998 |
| WO | WO 99/02194 | 1/1999 |
| WO | WO 99/02195 | 1/1999 |
| WO | WO 00/12147 | 3/2000 |

OTHER PUBLICATIONS

T.A. Fischell, "Radioactive Stents for the Prevention of Neointimal Hyperplasia", Physician's Press "The new manual of interventional cardiology", chapter 18, p. 134 ss (1996).
R. Makkar et al., "Technical and Engineering Aspects of Stents Which May be Either Permanent or Removable", *Endoluminal Stenting*, chapter 32, p. 230 (1996).
European Search Report, dated Mar, 22, 1999 for application EP 98100010 (2 pages).
*Textbook of Interventional Cardiology*, ed. Eric J. Topol, W.B. Saunders Company, 1994, and in particular Section IV of vol. II entitled "Coronary Stenting".
European Search Report for counterpart EP Application No. 99 83 0721 (2 pages).

*Primary Examiner*—Eric F. Winakur
*Assistant Examiner*—Nikita R Veniaminov
(74) *Attorney, Agent, or Firm*—Popovich & Wiles, PA

(57) ABSTRACT

A device, method, and kit for conveying a radioactive agent to a site of stenosis. The device includes a body portion to be disposed about the surface of a stent. The device comprises a radioactive agent. The device is capable of expanding, thus following the deployment movement of the stent, and is used to counter restenosis.

31 Claims, 3 Drawing Sheets

U.S. PATENT DOCUMENTS

| | | |
|---|---|---|
| 5,176,617 A | 1/1993 | Fischell et al. |
| 5,213,561 A | 5/1993 | Weinstein et al. |
| 5,342,283 A | 8/1994 | Good |
| 5,342,348 A | 8/1994 | Kaplan |
| 5,383,928 A | 1/1995 | Scott et al. |
| 5,395,300 A | 3/1995 | Liprie |
| 5,449,373 A | 9/1995 | Pinchasik et al. |
| 5,575,818 A | 11/1996 | Pinchuk |
| 5,605,530 A | 2/1997 | Fischell et al. |
| 5,632,771 A | 5/1997 | Boatman et al. ............ 623/1.34 |
| 5,637,113 A | 6/1997 | Tartaglia et al. |
| 5,674,242 A | 10/1997 | Phan et al. |
| 5,700,286 A | 12/1997 | Tartaglia et al. |
| 5,707,332 A | 1/1998 | Weinberger |
| 5,707,385 A | 1/1998 | Williams |
| 5,722,984 A | 3/1998 | Fischell et al. |
| 5,725,567 A | 3/1998 | Wolff et al. |
| 5,733,327 A | 3/1998 | Igaki et al. |
| 5,769,883 A | 6/1998 | Buscemi et al. |
| 5,776,184 A | 7/1998 | Tuch |
| 5,779,732 A | 7/1998 | Amundson |
| 5,840,008 A | 11/1998 | Klein et al. |
| 5,840,009 A | 11/1998 | Fischell et al. |
| 5,843,163 A | 12/1998 | Wall |
| 5,865,720 A | 2/1999 | Hastings et al. |
| 5,871,436 A | 2/1999 | Eury |
| 5,871,437 A * | 2/1999 | Alt ................................ 600/3 |
| 5,873,811 A | 2/1999 | Wang et al. |
| 5,919,163 A * | 7/1999 | Glickman .................... 604/101 |
| 5,942,209 A * | 8/1999 | Leavitt et al. ............. 424/1.25 |
| 6,013,099 A | 1/2000 | Dinh et al. |
| 6,071,227 A * | 6/2000 | Popowski et al. ............. 600/3 |
| 6,074,338 A * | 6/2000 | Popowski et al. ............. 600/3 |
| 6,129,757 A | 10/2000 | Weadock |
| 6,149,575 A * | 11/2000 | Leonharedt .................... 600/4 |
| 6,159,142 A | 12/2000 | Alt ................................ 600/3 |

\* cited by examiner

DEVICE FOR CONVEYING RADIOACTIVE AGENTS ON ANGIOPLASTY STENTS, RESPECTIVE METHOD AND KIT

FIELD OF THE INVENTION

This invention relates to stents for angioplasty, and in particular, relates to a device adapted to convey radioactive agents.

BACKGROUND OF THE INVENTION

The term "stent" is intended to indicate devices intended for endoluminal application (e.g., within a blood vessel), normally fitted via catheterization, with subsequent deployment in situ so as to provide a local supporting effect for the lumen.

For a general review of vascular stents reference may usefully be made to the work "Textbook of Interventional Cardiology" by Eric J. Topol, W.B. Saunders Company, 1994, and in particular section IV of Volume II entitled "Coronary stenting". A large number of patent documents have also been devoted to the subject, as evidenced by, for example, EP-A-0 806 190, EP-A-0 850 604, EP-A-0 847 766, EP-A-0 857 470, EP-A-0 875 215, EP-A-0 895 759 and EP-A-0 895 760.

Clinical use of such devices, which has developed appreciably in the course of the last few years, has to meet the need to ensure an effective action to counter the phenomenon currently known as restenosis. This is the phenomenon, associated with physiological mechanisms which are not yet wholly clear, as a result of which the site of the stenosis which is reopened through the effect of the stent implant tends gradually to close again, generally through the effect of gradual tissue growth.

Various arrangements that provide for developing an effect at local level which counters the phenomena giving rise to restenosis have been proposed in order to deal with this problem. In particular, various arrangements that provide for the local release of drugs or the local use of radioactive sources have been investigated. Arrangements based on local controlled release of drugs must, as a primary requirement, overcome the problem of effectively ensuring location at the site of the stent implant.

Arrangements that provide for the use of radioactive sources face a variety of difficulties. The main problems associated with the use of radioactive materials to counter restenosis are associated with distribution of the dose in the tissue and its decay over time. There are no radioisotopes having at the same time an energy and a type of radiation that can provide a uniform and effective dose in the first few millimeters of the wall but negligible at greater depths, a sufficiently long half-life to enable the radioisotope to be stored for a reasonable period of time (e.g., weeks) but which is sufficiently short not to permanently damage the vessel into which it is implanted; very high specific activity, and optimum biocompatibility.

However, there are partial solutions to the above problems. For example, phosphorus 32 has good characteristics in terms of half-life. Phosphorus 32 also can be obtained with high specific activities and can be implanted on the surface of the stent, but has low penetration (14 days, 1.7 MeV beta radiation). Palladium 103 has good half-life and penetration properties (17 days, 20 keV X-rays), but its specific activity is very low. Nevertheless, the use of enriched palladium obtained by irradiation in a reactor or through cyclotron irradiation starting from rhodium and performing a chemical separation have been suggested. The main disadvantage of this arrangement is in the relatively high cost of the material so obtained. Yttrium 90 has good penetration properties, but decays very quickly (64 hours, 2.2 MeV beta radiation). It has therefore been suggested that yttrium should be deposited on the stent a few hours before implantation, but this arrangement has appreciable problems and the possible effects in terms of biocompatibility have not yet been entirely clarified. Ruthenium 106 has excellent properties in terms of penetration, but lasts too long (1 year, 3.5 MeV beta radiation). Other radioisotopes, such as silver 105, have properties similar to palladium 103, and the same problems.

It can be said however, that the materials which are likely to have valuable properties with regard to having an effect which counters restenosis are poorly suitable, or not at all suitable, for producing the stent or parts thereof.

In every case the fact that the stent is rendered radioactive produces difficulties of a logistical type (implantation of the stent and the corresponding preparatory work are in fact of the nature of nuclear medicine activities), or unsatisfactory performance from the point of view of radioactive behavior.

The above-mentioned difficulties may perhaps explain why this research and investigation work has not yet resulted in effectively wide use of the corresponding methods. This irrespective of the fact that there is quite a large number of patent documents relating to the application of materials, in particular radioactive materials having an action which counters restenosis onto stents, or techniques substantially similar thereto. Among these documents, in addition to documents such as U.S. Pat. No. 5,059,166 (Fischell et al.); U.S. Pat. No. 5,176,617 (Fischell et al.) and U.S. Pat. No. 5,213,561 (Weinstein et al.) relating to the construction of radioactive stents, mention may be made of U.S. Pat. No. 5,722,984 (Fischell et al.), U.S. Pat. No. 5,840,009 (Klein et al.) and U.S. Pat. No. 5,605,530 (Fischell et al.) which refer to the application of substances such as phosphorylcholine labeled with phosphorus 32 to a stent, or means for overcoming the weakening of the dose at the ends of the stent through adding phosphorus 32 to the ends thereof, or again providing a screen to avoid the adverse effects of irradiation at the time when the stent is implanted.

Other documents such as WO-A-98/43694, WO-A-99/02195 or WO-A-99/09912 relate to coating a stent (or other means) with an antigen with a view to subsequent injection of a radioactive antibody, the application of a layer of radio-opaque material designed to receive the ionic implantation of radioactive material, or again a method of local treatment actuated by a device similar to a stent coated with a substance which is capable of reacting with another substance administered orally to generate in the locality a third substance which has a therapeutic effect.

U.S. Pat. No. 5,779,732 (Amundson) illustrates how a sheet of plastic containing a releasable substance can be located around a stent, while EP-A-0 873 732 discloses a stent coated with a substance which attracts heparin to form a layer of heparin.

Covering the wall of a vessel with an adhesive substance which is also radioactive is known from U.S. Pat. No. 5,873,811 (Wang et al.), while U.S. Pat. No. 5,871,436 (Eury) and U.S. Pat. No. 5,843,163 (Wall) describe how a radioactive substance can be fixed by means of a specific chelating agent or the use of a wire of radioactive material to keep an apertured stent extended.

WO-A-98/48851 teaches how a radioisotope can be applied to a metal stent: a very great number of isotopes are considered and the stents are of steel or shape memory metal (such as that sold under the trade designation "Nitinol"). Methods of application are electrochemical, of the electrodeless type, using peptides, fats or thiols. Yet other documents refer to brachytherapy techniques using radioactive sources temporarily located within the vessel: for example U.S. Pat. No. 5,865,720 (Hastings et al.) and U.S. Pat. No. 5,840,008 (Klein et al.) teach how a type of radioactive sheath or sleeve can be placed around a balloon. Furthermore, U.S. Pat. No. 5,707,332 (Weinberger) examines in detail all possible radioisotopes which could be used for brachytherapy, but finds none to be ideal. A source (liquid or gas) which is to be placed in the balloon, or a wire source which is moved forward and backwards in order to provide treatment as desired, is described.

SUMMARY OF THE INVENTION

This invention is a device or envelope for conveying a radioactive agent to a stenotic site. The envelope according to this invention can be applied to virtually any kind of stent, independently of, for example, the shape, type, technology of construction and method of expansion (balloon catheter, shape memory, etc.) of the stent itself and can be constructed using a variety of techniques depending upon the radioactive agent delivered and/or the performance required. Both the materials and the dimensions, and in particular the length, of the envelope are wholly independent—and may therefore also be markedly different—from the corresponding characteristics of the stent. For example, the envelope may be made to be shorter (or longer) than the stent, if this corresponds to an application requirement.

The device of this invention therefore makes both the choice and the method of dosing the radioactive agent wholly independent of the characteristics of the stent. In particular the choice of radioactive agent can be optimized and/or different doses of radioactive agent can be used in different parts of the stent. With the arrangement according to the invention it is even possible to deliver several different radioactive agents to one stent, for example to achieve different radiation characteristics in different areas of the stent and/or at different times following implantation of the stent.

A basic feature is provided by the fact that the arrangement according to the invention makes it possible to activate only the radioactive agent which has been delivered (at most together with the means delivering it), thus avoiding it being necessary to activate the stent itself, even in part.

The latter advantage is valuable for at least two reasons. First, the invention makes it possible to avoid activating the material comprising the stent. Usually activation of the stent as a whole gives rise to radiation phenomena which are difficult to control in relation to both dosage and the properties of the activated isotopes, and again in that it gives rise to mixed radiation resulting from various isotopes contained in the material forming the stent. Second, the device according to the invention is in fact capable of being associated with the stent only at the time of implantation and before such time may therefore follow a cycle of production, activation (usually by irradiation) and storage before and after activation which is wholly independent of the cycle for the production, distribution and storage of the stent.

In particular, the latter should not at any time be subjected to constraints imposed by the handling of radioactive material. All this with the further important advantage conferred by the fact that when a period of time has lapsed after activation of the device such that it can be considered that it has lost the desired level of radioactivity, only the device, and not, as is the case with traditional arrangements, the stent as well, and, furthermore, the introduction kit (balloon catheter, etc.) associated with it, need to be subjected to disposal. Above all, the arrangement according to the invention is also suitable for possible treatment to reactivate the device when this has lost its desired radioactive properties.

In one aspect, this invention is a device for conveying a radioactive agent onto a stent having a longitudinal axis and an inner surface and an outer surface, the stent being capable of being dilated from a radially-contracted position to a radially-expanded position, the device comprising a body portion having a longitudinal axis and an inner surface and an outer surface, the body portion configured to be disposed such that one of the inner and outer surfaces of the body portion is adjacent one of the inner and outer surfaces of the stent and capable of being dilated upon delivery of the stent at the stenotic site, the body portion comprising a material adapted to convey an effective amount of the radioactive agent to the stenotic site. The radioactive agent may be yttrium 90 and may be distributed non-uniformly within a matrix. The body portion preferably has a generally tubular shape. The body portion may comprise wire, and the wire may have a variable diameter. The body portion may be a sheet wound into a spiral, or it may have an apertured or reticular structure. Preferably, the inner surface of the body portion fits over the outer surface of the stent. The radioactive agent may comprise multiple components and may be in a particulate form, such as nanoparticles, within the matrix. The matrix may comprise fibers and/or may be erodible to permit gradual release of the radioactive material.

In a second aspect, this invention is a method of delivering a radioactive agent to a stenotic site comprising providing a stent having a longitudinal axis, an inner surface and an outer surface, the stent being capable of being dilated from a radially-contracted position to a radially-expanded position; providing a device comprising a body portion having a longitudinal axis and an inner surface and an outer surface, the body portion configured to be disposed such that a surface of the body portion is adjacent a surface of the stent and capable of being dilated upon delivery of the stent at the stenotic site, the body portion comprising a material adapted to convey an effective amount of the radioactive agent to the stenotic site; advancing the stent and the device through a patient's vasculature to the site of stenosis; and dilating the stent and the device at the site of stenosis such that a surface of the body portion of the device is positioned adjacent a surface of the stent. The dilating step may comprise positioning the surface of the body portion of the device adjacent the outer surface of the stent. The stent may be formed from a tubular blank.

In a third aspect, this invention is a kit for conveying a radioactive agent onto a stent having a longitudinal axis and an inner surface and an outer surface, the stent being capable of being dilated from a radially-contracted position to a radially-expanded position, the kit comprising a device comprising a body portion having a longitudinal axis and an inner surface and an outer surface, the body portion configured to be disposed such that one of the surfaces of the body portion is adjacent a surface of the stent and capable of being dilated upon delivery of the stent at the stenotic site, the body portion comprising a material adapted to convey an effective amount of the radioactive agent to the stenotic site; and a container configured to house the device. The kit may further comprise the stent and a catheter adapted to deliver the stent and the device to the site of restenosis.

BRIEF DESCRIPTION OF THE DRAWINGS

The invention will now be described purely by way of a non-restrictive example with reference to the appended drawings.

DETAILED DESCRIPTION OF THE PREFERRED EMBODIMENTS

Figure 1:
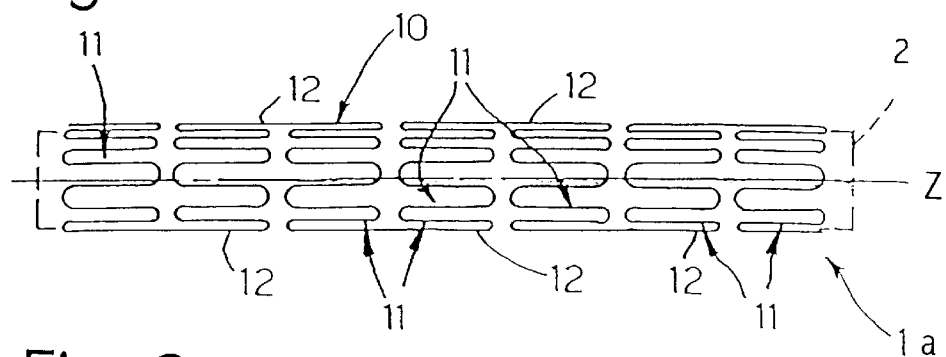
FIG. 1 illustrates a diagrammatic view of one embodiment of the invention.

In the figures, reference numbers 1a to 11 indicate a device according to the invention. For the sake of simplicity, reference number 1 will refer generally to the device of this invention and reference number 2 will refer to the stent. Device or envelope 1 comprises radioactive materials. For the reasons illustrated in the introductory part of this description, this objective is pursued so as to associate an action countering restenosis with the stent. At least in principle the possible applications of the invention will not however be regarded as being restricted exclusively to this purpose.

The profile of stent 2 with which device 1 is associated is indicated diagrammatically. In all the figures, which are viewed from the side (FIGS. 1 to 3, 5 to 6 and 8 to 10), or seen in approximately lateral perspective view (FIGS. 4, 7, 11 and 12), the stent is illustrated in the radially contracted condition and is shown essentially as a small tube of cylindrical shape.

This approach, which is deliberately diagrammatical, has been adopted to point out the fact that the device according to the invention can be used in practice with any type of stent, independently of its shape, structural, construction and expansion characteristics. Reference number 2 is used to refer to the stent shown in the figures, and it is to be understood that stent 2 may have characteristics that correspond to the great variety of stents known in the art, which makes it unnecessary to mention these characteristics, even merely by way of example. This also applies to the means, methods and criteria used to achieve deployment of the stent in its site of implantation (dilation by means of a balloon catheter, construction of self-expanding stents, e.g., through the use of materials having shape memory, etc.).

The figures relate to arrangements in which stent 2 is a small tube having a diameter which is slightly less than and a length which is slightly greater than that of envelope or device 1. This representation is however purely by way of example, given that the length of envelope 1 may be both less than, the same as or even greater than that of stent 2. It is not necessary that the shape of envelope 1 should precisely copy the shape of the stent: notwithstanding, of course, the requirement for physical compatibility between the shapes, both stent 2 and envelope 1 may have, for example, cross sections which vary along their longitudinal length, and therefore narrow portions, wide portions, parts having a cross section other than a circular cross section, etc.

The arrangements to which FIGS. 1 to 12 refer provide that envelope 1 should be fitted on, that is located, outside stent 2. This arrangement, which at the present time is regarded as being preferred (both because of the possibility that deployment and anchorage of envelope 1 at the site can be achieved automatically through the effect of the deployment of stent 2, and because it is generally desired to encourage the radiation to act towards the walls of the vessel in which stent 2 is implanted), is not however mandatory. The invention therefore also relates to embodiments in which envelope 1 is intended to be fitted within stent 2, with suitable forms of radial anchorage being provided for this purpose.

The arrangement illustrated in the figures, in which envelope 1 is fitted on the outside of stent 2, has proved to be particularly advantageous from the point of view of use in that it makes it possible to associate envelope 1 with stent 2 immediately before the operation of implantation.

Envelope or device 1 may be provided in kit form; that is, placed in a container or package. The envelope can therefore be taken from the corresponding protective container by the same person who is performing the implant, to be fitted over and "crimped" onto the desired stent immediately before the implanting operation. Alternatively, an implant kit may comprise stent 2 and associated envelope 1 (normally already activated), with the possibility of stent 2 being placed on the corresponding implantation catheter (of a known type).

Examination of FIGS. 1 to 12 will show how the device according to the invention is designed to convey a material capable of exerting an effective radioactive effect at the site of the stent implant. This is realized wholly or in part using such material or by delivering bodies comprising such material.

The words "material capable of exerting an effective radioactive effect at the site at which the stent is implanted" are designed to shed light on some significant aspects of the arrangement according to the invention. That is, although a different arrangement should not be ruled out (at least in principle), the aforesaid material does not yet have any radioactive effect at the time when it is used to manufacture the device or is associated as a constituent part of envelope 1 itself. Normally the radioactive properties are imparted subsequently, for example, by irradiation from a source of radiation (typically in a nuclear reactor). The level of radioactivity imparted to the envelope is that appropriate for the context of the application in question, that is, is sufficient to achieve an effective action to counter restenosis.

By way of example reference may be made to the various energy levels and types of radiation to which reference is made in the introductory part of the description. The radiation may be, for example, X-rays having an energy of the order of 18–25 keV (kilo electron volts), which are not substantially attenuated in the first few millimeters of penetration. Another advantageous choice is a high energy beta ray emitter such as yttrium 90. In this case it would be conceivable to use a Sr90/Y90 generator to produce envelope 1 which is intended to be delivered to a hospital within 1–2 days for use if appropriate in association with a corresponding stent in an implant kit.

In any event, the arrangement according to the invention is ideally suited to the possibility of coordinating the structure and construction technology of envelope 1 with the choice of radioactive material (it will be remembered that this material can in reality also comprise several radioactive isotopes). For example, the radioactive material may be in the form of a wire or plate for use in combination with radioactive materials having ductility or malleability properties, or incorporation in a matrix in the presence of radioactive materials available in powder form. The arrangement according to the invention is also suitable for use in combination with a binding agent-ligand association, where either the binding agent or the ligand is initially applied to envelope 1, and then the ligand or the binding agent comprises the radioactive material which is to be introduced (typically injected) into the patient to bind on the envelope 1 implanted together with the corresponding stent.

Figure 8:
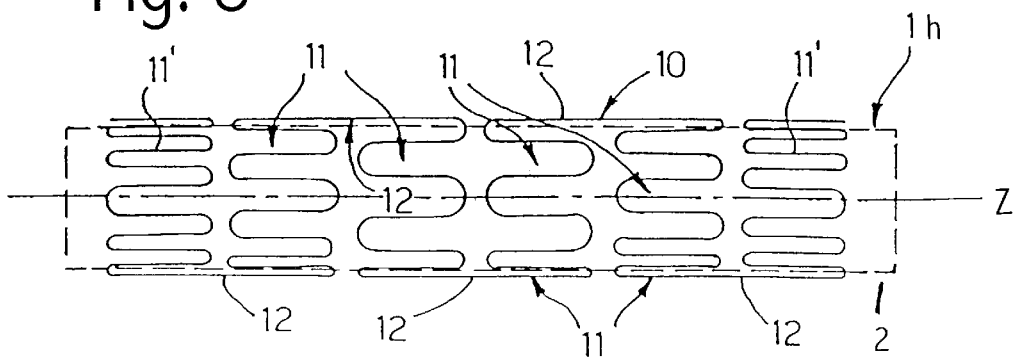
FIGS. 8 and 9 illustrate diagrammatic views of alternate embodiments of the device shown in FIG. 1.
Figure 9:
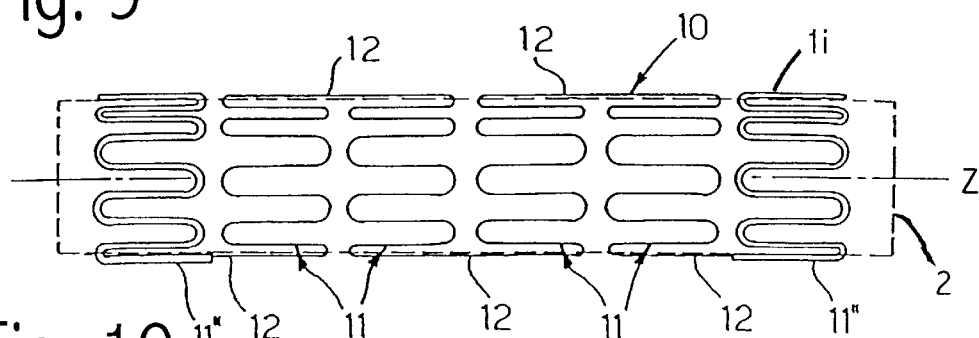

FIGS. 1, 8 and 9 illustrate envelopes 1a, 1h, and 1i in the form of a tubular body (which on the whole can be likened to a stent in its structure) constructed from a wire-like material 10. Material 10 comprises a material that is capable of being rendered radioactive. Also bearing in mind the quantity of material (10 to 20 mg) which is likely to be used to construct envelopes 1a, 1h, and 1i, this may also be (for example) palladium, so that sufficient total activity can be provided without resorting to enriched palladium.

The wire-shaped material in question (which is capable of adopting the appearance of a plate, at least locally) is wound into a shape to give rise to a set of sections 11 of generally cylindrical shape in the form of a coil, connected together by lengths of wire 12 which extend in the direction of the generatrices of the cylindrical linear surface (i.e., longitudinal axis Z) over which envelope 1 extends. The corresponding manufacturing technology should be regarded as being well known, particularly in the field of stents: in this respect reference may be made to, for example, European patent application EP-A-0 806 190.

As described above, in the embodiments shown in FIGS. 1, 8 and 9, envelopes 1a, 1h, and 1i may only be partly constructed of material capable of being made radioactive; for example, with reference to FIG. 1, in the form of wires of material that can be made radioactive. For example, the wires can be woven or braided into a structure similar to that illustrated in FIG. 1.

The embodiments shown in FIGS. 8 and 9 illustrate that by acting on the structural features of envelopes 1h and 1i it is possible to obtain a change in the density of the constituent material along the longitudinal length of the envelope, with a consequent possible variation in the radioactivity properties which can be achieved through the envelopes 1h and 1i.

For example, FIG. 8 relates to an embodiment in which, while retaining the coil arrangement, the end sections 11' of envelope 1i are constructed having a sinusoidal shape with a smaller period (that is, figuratively speaking, a higher "frequency") in comparison with sections 11 which are located at the center of envelope 1h. All this has the effect that more material capable of being made radioactive is present in these end sections 11'.

In this way, when the material is activated and rendered radioactive, it is possible to achieve an effect varying the level of local radiation with respect to adjacent zones in these end zones. This arrangement can also be adopted asymmetrically, so that single section 11', in which the wire is present in a condensed form, is present at one end of envelope 1h, with a different number of similar sections (i.e., two sections 11') at the other end. Of course this density effect (or rarefaction effect, achieved by increasing the pitch of the winding of the wire coil) can be achieved selectively in any portion of the longitudinal extent of envelope 1h. The action of varying/modulating radioactive activity may also be achieved by different means, for example, using different radioisotopes and/or different radioactivity properties in different portions of the stent.

The abovementioned variation/modulation effect may be made use of for different purposes. For example, the fact of increasing the level of local radioactivity at the ends of device or envelope 1 can be utilized for at least two purposes:

(1) ensuring a uniform level of radioactivity along the entire longitudinal length of envelope 1 (for the same linear density of radioactive material the intensity of the radiation determined along the principal longitudinal axis Z of envelope 1 has a maximum value at the center and a minimum value at the ends), and/or (2) achieving maximum radioactivity values at the ends of envelope 1, therefore corresponding to the ends of stent 2 over which it is fitted.

This latter arrangement is advantageous when it is desired to counter the phenomena of restenosis which sometimes occur at the ends of the site where the stent is implanted, where the walls of the vessel are no longer supported and held apart by the stent itself.

By contrast, FIG. 9 shows a variant in which the two end sections, indicated by 11", are made of wire of different diameter (e.g., greater diameter) and/or different cross section (e.g., using a flattened transverse profile). In this case also a symmetrical or asymmetrical arrangement is possible at the two ends of envelope 1i or, in general, in any region along the longitudinal extent of the means.

Figure 2:
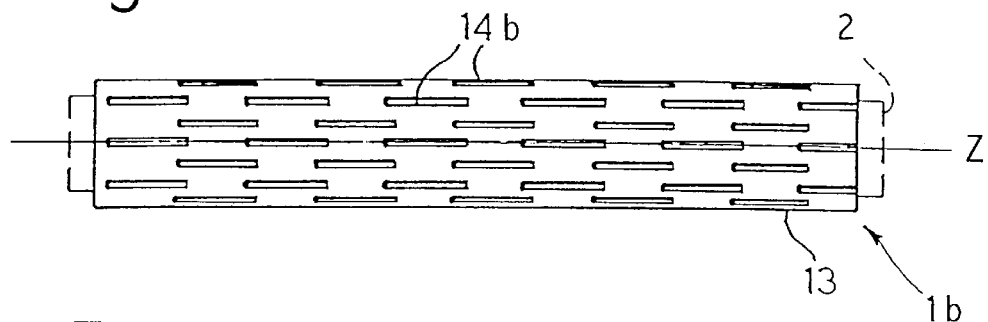
FIG. 2 illustrates a diagrammatic view of a second embodiment of the invention.
Figure 3:
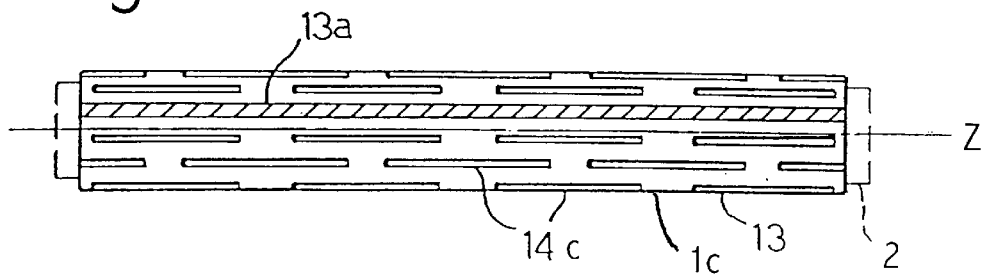
FIG. 3 illustrates a diagrammatic view of a third embodiment of the invention.
Figure 4:
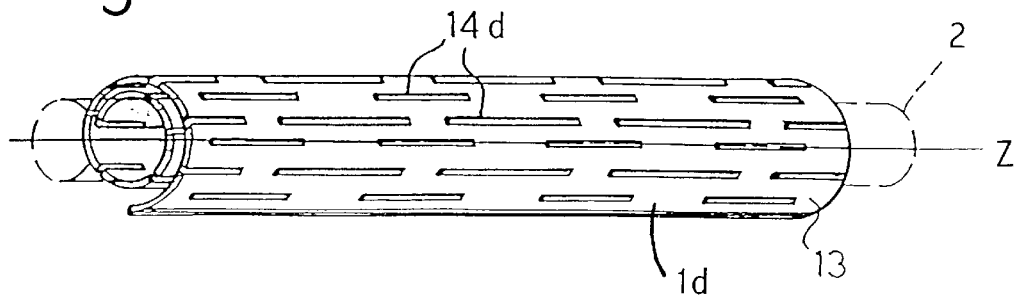
FIG. 4 illustrates a perspective view of a fourth embodiment of the invention.

FIGS. 2 and 4 relate to arrangements that provide for producing envelopes 1b and 1d in the form of a tubular body 13 of, for example, metal. This may then take the form of both a body which is already of a tubular shape (FIG. 2) or a flat sheet which is curved and closed to form a tube using a longitudinal weld 13a (FIG. 3), or again a sheet which is merely wound on itself in accordance with a generally spiral arrangement (FIG. 4). A sheet may be capable of maintaining a closed configuration either through intrinsic plasticity properties (possibly associated with shape-memory properties) or because it is constrained by retaining members — not illustrated, but of a known type—whose action is reduced at the time when the stent is dilated.

These embodiments are obviously suitable for use with particular advantage in combination with materials which can be rendered radioactive and which have good malleability properties.

As illustrated in FIGS. 2 and 3, the open structure that is necessary to ensure that envelopes 1b and 1c follow the expansion movement of stent 2 is achieved by forming openings in the form of slots 14b and 14c. This apertured structure has also been shown, as it is preferred, in connection with the embodiment in FIG. 4, having slots 14d. At least in principle, sheet 13 illustrated therein is capable of being wound on itself to follow the expansion movement of the stent. The open structure deriving from the presence of slots 14b, 14c, or 14d is however such as to render sheet 13 deformable, and therefore extendible.

Manufacturing techniques (laser cutting or EDM or chemical etching, etc.) which can be applied to the construction of the embodiments shown in FIGS. 2 to 4 are in general known in the technology of stent manufacture and do not need to be illustrated specifically here.

Also with reference to what will be said below, emphasis is again placed on the fact that the material which can be made radioactive may be a single well-defined isotope, a mixture of two or more isotopes intended to provide different radiation properties, or an alloy material containing one or more materials which are capable of being made radioactive among its components. As already mentioned, the variation in the type or types of the radioactive materials used makes it possible to achieve an effect modulating/varying the radiation characteristics in various sections or portions of the envelope, and therefore of the stent with which it is associated.

The embodiments in FIGS. 5 to 7 and 10 are suitable for being implemented in a particularly advantageous form when the material which is capable of being rendered radioactive (again in this case a single isotope, a mixture of two or more isotopes, or a material which incorporates such an isotope or isotopes) is present in the form of particles (such as powder or micropowder). This is typically the situation for a material such as ruthenium.

In this case envelopes 1e, 1f, 1g, and 1j may comprise a matrix 15e, 15f, 15g, and 15j, respectively. The matrix is, for example, a small tube of extendible synthetic material (e. g., silicone) within which radioactive material 16 is dispersed. Matrices 15e, 15f, 15g, and 15j may possibly have erodability and/or consumability properties such that it gives rise to slow release of material 16 (with consequent distancing from the site of implantation).

Figure 5:
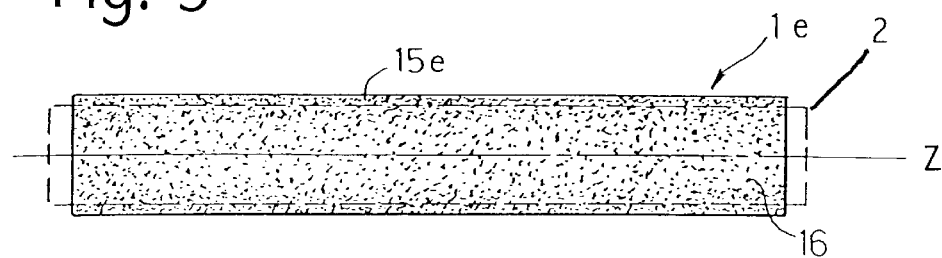
FIG. 5 illustrates a diagrammatic view of a fifth embodiment of the invention.
Figure 10:
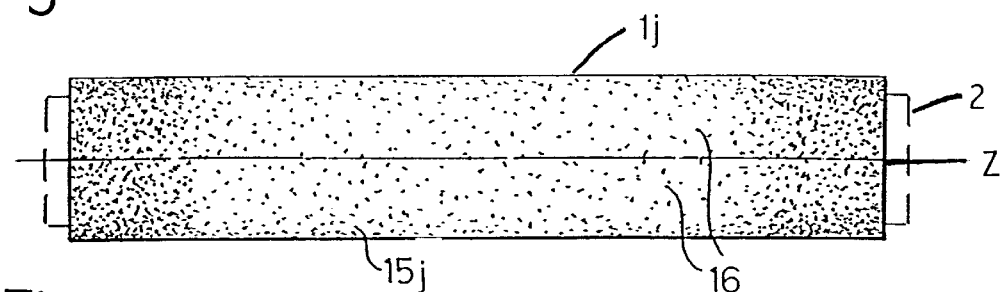
FIG. 10 illustrates a diagrammatic view of an alternate embodiment of the device shown in FIG. 5.

In this case too the dispersion of material 16 in the matrix may be uniform, as shown in FIG. 5, or have the features of a differential density along the length of envelope 1j, as shown in FIG. 10. In particular, the latter figure shows an arrangement which in many respects is similar to those shown in FIGS. 8 and 9, that is an arrangement in which the density of the distribution of radioactive material 16 in particle form is differentiated in such a way as to obtain a more marked local radioactive effect at the ends of envelope 1. As already mentioned, this result could also be achieved by acting on the type and the nature of material 16.

Figure 6:
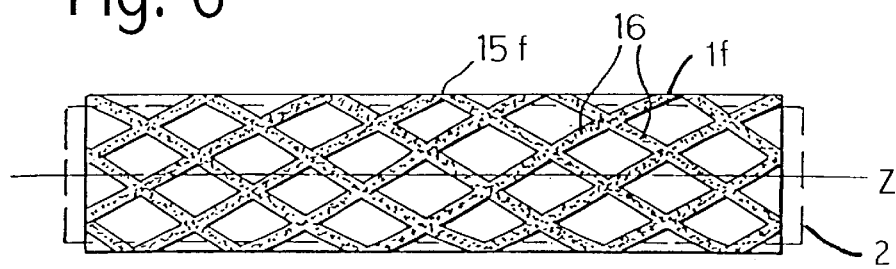
FIG. 6 illustrates a diagrammatic view of a sixth embodiment of the invention.

In the arrangement in FIG. 6, matrix 15f has a structure which is no longer compact, but apertured, for example of a reticular nature. This result may be obtained by starting from a compact tubular body, which is apertured for example by forming openings or notches (the rhomboidal shape of the mesh illustrated in FIG. 6 is purely by way of example), or by weaving wires or fibers (e.g., of synthetic material such a silicone) in a general mesh structure.

The fibers in question may be fibers of the type described in commonly assigned, co-pending U.S. patent Ser. No. 09/632,042, entitled "An Angioplasty Stent Adapted to Counter Restenosis, Respective Kit, and Component", hereby incorporated herein in its entirety by reference. The fibers may comprise associated particles or nanoparticles of materials which can be rendered radioactive, possibly with the properties of erodability. Such particles or nanoparticles are preferably substantially spherical in shape. Nanoparticles have diameters ranging up to about several hundred nanometers, for example, up to about 500 nanometers.

Figure 7:
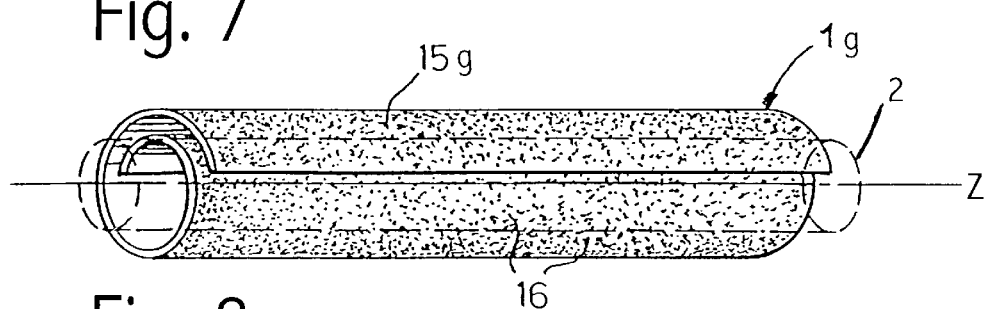
FIG. 7 illustrates a perspective view of a seventh embodiment of the invention.

FIG. 7 shows a further possible variant which combines, so to speak, features from the arrangement in FIG. 5 (use of a envelope 1e (FIG. 5) and envelope 1g (FIG. 7)) in which material 16 which can be made radioactive is dispersed) with features of the arrangement in FIG. 4, in which envelope 1d is produced from a sheet wound into a coil. For the reasons already mentioned in connection with the embodiment in FIG. 5, in the case of the embodiment in FIG. 7 it is not strictly required that the sheet comprising matrix 15g should have extendibility properties.

Figure 11:
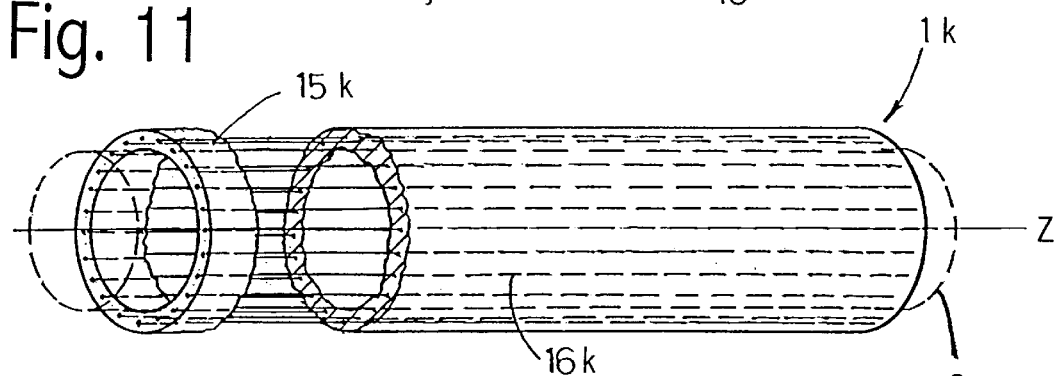
FIGS. 11 and 12 illustrate perspective views of two further embodiments of the invention.
Figure 12:
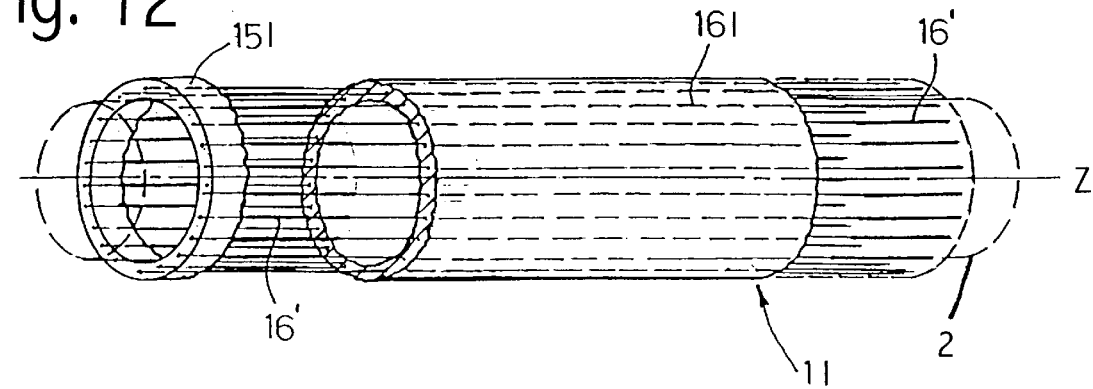

The same also applies in substance to the reticular embodiment in FIG. 6, where the properties of radial expandability can be provided through the effect of the geometry of the mesh, even if the members of such meshes (e.g., the fibers forming the braiding for envelope 1) do not in themselves have the property of being able to extend longitudinally. The other variants illustrated in FIGS. 11 and 12 can be regarded as deriving from the combination of teachings in FIGS. 5, 7 and 10 with the teachings in FIGS. 1 and 9. In the case of FIGS. 11 and 12, material 16k or 16l dispersed in matrices 15k or 15l, respectively, takes the form of wires, which may have different structural geometrical and/or composition properties in the various regions of device or envelope 1. In the example in FIG. 12 the difference is illustrated by showing ends of wires indicated by 16' which have a different diameter/shape from the remainder of the wires.

From the foregoing illustrations it is clear that the various principles of construction illustrated with reference to FIGS. 1 to 12 can also be used in combinations other than those illustrated, in particular as regards the possibility of using different radioactive materials in envelope 1. For example, the embodiment in FIG. 6 may be obtained by using metal wires that are only partly coated with polymers or elastomers within which a material which can be made radioactive is dispersed.

Of course, without changing the principle of the invention, the details of construction and embodiments can be varied extensively from what has been described and illustrated without thereby going beyond the scope of this invention as defined by the following claims.

What is claimed is:

1. A device for conveying a radioactive agent onto a stent having a longitudinal axis and an inner surface and an outer surface, the stent being capable of being dilated from a radially-contracted position to a radially-expanded position, the device comprising:

a body portion having a longitudinal axis and an inner surface and an outer surface, the body portion configured to be disposed such that the outer surface of the body portion is adjacent the inner surface of the stent and configured to be dilated upon delivery of the stent at the stenotic site, the body portion comprising a material adapted to convey an effective amount of the radioactive agent to the stenotic site.

2. The device of claim 1 wherein the radioactive agent is yttrium 90.

3. The device of claim 1 wherein the body portion has a generally tubular shape.

4. The device of claim 1 wherein the body portion comprises wire having a diameter.

5. The device of claim 4 further wherein the body portion has first and second sections and wherein the diameter of the wire comprising the first section is different than the diameter of the wire of comprising the second section.

6. The device of claim 1 wherein the body portion comprises a sheet wound into a spiral.

7. The device of claim 1 wherein the body portion has an apertured structure.

8. The device of claim 1 wherein the body portion has a reticular structure.

9. The device of claim 1 wherein the radioactive agent comprises multiple components.

10. The device of claim 1 wherein the body portion comprises a matrix containing the radioactive agent.

11. The device of claim 10 wherein the radioactive agent is distributed nonuniformly within the matrix.

12. The device of claim 10 wherein the radioactive agent is in particulate form within the matrix.

13. The device of claim 12 wherein the particulate form is nanoparticles.

14. The device of claim 10 wherein the matrix comprises fibers.

15. The device of claim 10 wherein the matrix is erodible so as to permit gradual release of the radioactive material.

16. A method of delivering a radioactive agent to a stenotic site comprising:

providing a stent having a longitudinal axis, an inner surface and an outer surface, the stent being capable of being dilated from a radially-contracted position to a radially-expanded position;

providing a device comprising a body portion having a longitudinal axis and an inner surface and an outer surface, the body portion configured to be disposed such that the outer surface of the body portion is adjacent the inner surface of the stent and capable of being dilated upon delivery of the stent at the stenotic site, the body portion comprising a material adapted to convey an effective amount of the radioactive agent to the stenotic site;

advancing the stent and the device through a patient's vasculature to the site of stenosis; and dilating the stent and the device at the site of stenosis such that a surface of the body portion of the device is positioned adjacent a surface of the stent.

17. The method of claim 16 wherein the radioactive agent is yttrium 90.

18. The method of claim 16 wherein the step of providing the stent further comprises providing the stent comprising a sheet formed into a tubular structure.

19. The method of claim 16 wherein the step of providing the stent further comprises providing the stent formed from a tubular blank.

20. A kit for conveying a radioactive agent onto a stent having a longitudinal axis and an inner surface and an outer surface, the stent being capable of being dilated from a radially-contracted position to a radially-expanded position, the kit comprising:

a body portion having a longitudinal axis and an inner surface and an outer surface, the body portion configured to be disposed such that the outer surface of the body portion is adjacent the inner surface of the stent and configured to be dilated upon delivery of the stent at the stenotic site, the body portion comprising a material adapted to convey an effective amount of the radioactive agent to the stenotic site; and a container configured to house the device.

21. The kit of claim 20 further comprising the stent.

22. The kit of claim 21 further comprising a catheter adapted to deliver the stent and the device to the site of restenosis.

23. The kit of claim 20 wherein the inner surface of the device is configured to be disposed over the outer surface of the stent.

24. The kit of claim 20 wherein the radioactive agent is yttrium 90.

25. A device for conveying a radioactive agent having a radioactive property onto a stent having a longitudinal axis and an inner surface and an outer surface, the stent being capable of being dilated from a radially-contracted position to a radially-expanded position, the device comprising:

a body portion having first and second ends, a longitudinal axis and an inner surface and an outer surface, the body portion configured to be disposed such that one of the inner and outer surfaces of the body portion is adjacent one of the inner and outer surfaces of the stent and configured to be dilated upon delivery of the stent at the stenotic site, the body portion comprising a material adapted to convey an effective amount of the radioactive agent to the stenotic site, the amount of radioactive agent conveyed by the body portion being dependent on the density of the material comprising the body portion, the material having a first density along a first section of the body portion and a second density along a second section of the body portion, the first density being different from the second density, such that the amount of radioactive agent conveyed by the first section is different than the amount of radioactive agent conveyed by the second section.

26. The device of claim 25 wherein the first section comprises a tubular coil with a sinusoidal shape having a first frequency and the second section comprises a tubular coil with a sinusoidal shape having a second frequency, the first frequency being different from the second frequency.

27. The device of claim 25 wherein the first section comprises a wire having a first cross-section and forming a tubular coil with a sinusoidal shape, and the second section comprises a wire having a second cross-section and forming a tubular coil with a sinusoidal shape, the first cross-section being different from the second cross-section.

28. The device of claim 25 wherein the first section comprises a matrix containing the radioactive agent and the second section comprises a matrix containing the radioactive agent, and wherein the density of the radioactive agent in the first section is different than the density of the radioactive agent in the second section.

29. A device for conveying a radioactive agent to a site within a vessel where a stent is deployed for the purpose of imparting to the site a level of local radioactivity, the stent having a longitudinal axis and an inner surface and an outer surface, the stent being capable of being dilated from a radially-contracted delivery position to a radially-expanded deployed position, the device comprising:

a body portion having first and second ends, a longitudinal axis and an inner surface and an outer surface, the body portion configured to be disposed such that one of the inner and outer surfaces of the body portion is adjacent one of the inner and outer surfaces of the stent when the stent is in the deployed position within the vessel, the body portion having a first section having a first density of radioactive agent for imparting a first level of local radioactivity and a second section having a second density of radioactive agent for imparting a second level of local radioactivity, the first level of radioactivity being greater than the second level of radioactivity.

30. The device of claim 29 wherein the first section comprises a tubular coil with a sinusoidal shape having a first frequency and the second section comprises a tubular coil with a sinusoidal shape having a second frequency, the first frequency being greater than the second frequency.

31. The device of claim 29 wherein the first section comprises a wire having a first cross-section and forming a tubular coil with a sinusoidal shape, and the second section comprises a wire having a second cross-section and forming a tubular coil with a sinusoidal shape, the first cross-section being greater than the second cross-section.

* * * * *